United States Patent
Geertman et al.

(10) Patent No.: US 11,066,688 B2
(45) Date of Patent: Jul. 20, 2021

(54) METHOD FOR PREPARING A STEVIOL GLYCOSIDE COMPOSITION

(71) Applicant: DSM IP ASSETS B.V., Heerlen (NL)

(72) Inventors: Robert Geertman, Echt (NL); Igor Galaev, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 183 days.

(21) Appl. No.: 15/742,561

(22) PCT Filed: Jul. 11, 2016

(86) PCT No.: PCT/EP2016/066444
§ 371 (c)(1),
(2) Date: Jan. 8, 2018

(87) PCT Pub. No.: WO2017/009294
PCT Pub. Date: Jan. 19, 2017

(65) Prior Publication Data
US 2018/0371516 A1  Dec. 27, 2018

Related U.S. Application Data

(60) Provisional application No. 62/191,007, filed on Jul. 10, 2015.

(51) Int. Cl.
| | |
|---|---|
| C12P 19/56 | (2006.01) |
| A23L 27/30 | (2016.01) |
| C12P 19/44 | (2006.01) |
| A23L 33/20 | (2016.01) |
| A23L 2/60 | (2006.01) |

(52) U.S. Cl.
CPC ............... *C12P 19/56* (2013.01); *A23L 2/60* (2013.01); *A23L 27/30* (2016.08); *A23L 27/36* (2016.08); *A23L 33/20* (2016.08); *C12P 19/44* (2013.01)

(58) Field of Classification Search
CPC .......... A23L 27/30; A23L 33/20; A23L 27/36; A23L 2/60; C12P 19/56; C12P 19/44
USPC .......... 426/548, 650, 49, 478, 490, 492, 495
See application file for complete search history.

(56) References Cited

U.S. PATENT DOCUMENTS

2014/0255579 A1   9/2014   Nachfolger et al.
2016/0213039 A1   7/2016   Kumar et al.

FOREIGN PATENT DOCUMENTS

| | | |
|---|---|---|
| CN | 101200480 A | 6/2008 |
| CN | 101220062 A | 7/2008 |
| CN | 102250167 A | 11/2011 |
| CN | 102250990 A | 11/2011 |
| CN | 102286041 A | 12/2011 |
| JP | S56121453 A | 9/1981 |
| JP | H02261359 A | 10/1990 |
| WO | 2011/153378 A1 | 12/2011 |
| WO | 2012/082493 A1 † | 6/2012 |
| WO | 2015/014969 A1 | 6/2012 |
| WO | 2014/086890 A1 † | 6/2014 |
| WO | 2015/014969 A1 † | 2/2015 |
| WO | 2016/130609 A1 † | 8/2016 |

OTHER PUBLICATIONS

Martono, Yohanes et al., "Water-based crystallization and formulation of Stevioside from Stevia rebaudiana (Bert.) as a natural sweetener with antidiabetic activity," (Dec. 2012), XP002760704, pp. 1-8.
Anonymous, "Manufacturing of our products," Sucrevia, (Jan. 19, 2012), XP002760705, pp. 1-2.
Database WPI, Week 201213, Thompson Scientific, London, GB, AN 2011-Q34574, XP002702395.
Liu, J. et al., "Subcritical Fluid Extraction of Stevia Sweetners from Stevia rebaudiana," Journal of Chromatographic Science, (Sep. 1, 1997), XP055294767, vol. 35, No. 9, pp. 446-450.
Parashar, Bharat et al., "Stevia (Meethi patti): Prospects As an Emerging Natural Sweetener," International Journal of Pharmaceutical and Chemical Sciences, (Mar. 1, 2013), XP055294778, pp. 214-225.
International Search Report in corresponding application No. PCT/EP2016/066444 dated Aug. 30, 2016.
Third Party Observation of European Patent Application No. 20160738144 dated Sep. 2019.

† cited by third party

*Primary Examiner* — Leslie A Wong
(74) *Attorney, Agent, or Firm* — McBee Moore & Vanik IP, LLC

(57) ABSTRACT

The present invention relates to a composition comprising one or more steviol glycosides which composition comprises nitrogen in an amount of no more than about 1000 ppm. The invention also relates to a method for preparing a steviol glycoside composition, which method comprises: providing a steviol glycoside composition; combining the steviol glycoside composition with water to form a steviol glycoside solution; and crystallizing a steviol glycoside composition from the solution. The invention also relates to a method for reducing the nitrogen content of a steviol glycoside composition, which method comprises: providing a steviol glycoside composition which comprises nitrogen; combining the steviol glycoside composition with water to form a steviol glycoside solution; and crystallizing a steviol glycoside composition from the solution, thereby to reduce the amount of nitrogen in the steviol glycoside composition.

14 Claims, No Drawings

METHOD FOR PREPARING A STEVIOL GLYCOSIDE COMPOSITION

CROSS REFERENCE TO RELATED APPLICATIONS

This application is a National Stage entry of International Application No. PCT/EP2016/066444 filed 11 Jul. 2016, which claims priority to U.S. Provisional Application No. 62/191,007, filed 10 Jul. 2015.

BACKGROUND

Field of the Invention

The present invention relates to a composition comprising one or more steviol glycosides. The invention also relates to a method for purifying a steviol glycoside composition.

Description of Related Art

The leaves of the perennial herb, Stevia rebaudiana Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in Stevia leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in Stevia leaves. It may be about 200 times sweeter than sucrose. Rebaudioside M is a further high-potency diterpene glycoside sweetener. It is present in trace amounts in certain stevia variety leaves, but has been suggested to have a superior taste profile.

Steviol glycosides have traditionally been extracted from the Stevia plant. In Stevia, (−)-kaurenoic acid, an intermediate in gibberellic acid (GA) biosynthesis, is converted into the tetracyclic dipterpene steviol, which then proceeds through a multi-step glycosylation pathway to form the various steviol glycosides. However, yields may be variable and affected by agriculture and environmental conditions. Also, Stevia cultivation requires substantial land area, a long time prior to harvest, intensive labour and additional costs for the extraction and purification of the glycosides.

More recently, therefore, interest has grown in producing steviol glycosides using fermentative processes. WO2013/110673 and WO2015/007748 describe microorganisms that may be used to produce at least the steviol glycosides rebaudioside A and rebaudioside D.

Methods are required to isolate steviol glycosides from such fermentative processes, for example to take into account the accumulation of compounds in fermentation broths that may not be present in plant derived compositions of steviol glycosides.

SUMMARY

The present invention is based on the identification of a process for recovery of steviol glycosides, for example from fermentation broths, wherein the resulting steviol glycoside composition comprises low or no amounts of nitrogen.

Accordingly, the invention relates to a composition comprising one or more steviol glycosides which composition comprises nitrogen. However, the nitrogen is present in an amount of nitrogen of no more than about 1000 ppm, no more than about 500 ppm, no more than about 100 ppm or no more than about 50 ppm. That is to say, the invention relates to a composition comprising one or more steviol glycosides and nitrogen, wherein the amount of nitrogen is no more than about 1000 ppm, no more than about 500 ppm, no more than about 100 ppm or no more than about 50 ppm Typically, the composition will comprise a high amount, such as at least about 95% by dry weight, of one steviol glycoside, such as rebaudioside A, rebaudioside D or rebaudioside M.

The invention also relates to:
a method for preparing, for example purifying, a steviol glycoside composition, which method comprises crystallizing steviol glycosides from an aqueous solution comprising steviol glycosides;
a method for reducing the nitrogen content of a steviol glycoside composition, which method comprises crystallizing steviol glycosides from an aqueous solution comprising steviol glycosides and nitrogen;
a method for preparing a steviol glycoside composition, which method comprises:
providing a steviol glycoside composition;
combining the steviol glycoside composition with water to form a steviol glycoside solution; and
crystallizing a steviol glycoside composition from the solution; and
a method for reducing the nitrogen content of a steviol glycoside composition, which method comprises:
providing a steviol glycoside composition which comprises nitrogen;
combining the steviol glycoside composition with water to form a steviol glycoside solution; and
crystallizing a steviol glycoside composition from the solution, thereby to reduce the amount of nitrogen in the steviol glycoside composition.

Further, the invention relates to a steviol glycoside composition obtainable by a method of the invention.

DETAILED DESCRIPTION OF A PREFERRED EMBODIMENT

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

Herein, a steviol glycoside composition means a composition comprising one or more steviol glycosides and a steviol glycoside solution is a solution comprising one or more steviol glycosides.

The invention relates to a method for purifying steviol glycosides, for example from a fermentation broth which comprises one or more steviol glycosides produced by a microorganism. Such a microorganism would typically be a recombinant microorganism which has been modified such that it is capable of producing one or more steviol glycosides. The invention also relates to compositions produced by such a process.

Steviol glycoside compositions are typically purified using ethanol (or other organic solvent):water crystallizations. We have found that when using this type of crystallization for purification of fermentatively derived steviol glycoside compositions, final nitrogen levels may be in excess of 1000 ppm. The origin of such nitrogen may be as cells partially lyse during and/or after fermentation. We have further found that this nitrogen may substantially be removed by an additional recrystallization, i.e. polish crystallization step, which is carried out in water.

A composition of the invention comprises one or more steviol glycosides. In addition, a composition of the invention comprises nitrogen. However, the composition comprises nitrogen in an amount of no more than about 1000 ppm. That is to say, a composition of the invention comprises a non-zero amount of nitrogen up to a maximum amount of about 1000 ppm.

A composition of the invention may comprise up to about 900 ppm, up to about 800 ppm, up to about 700 ppm, up to about 600 ppm, up to about 500 ppm, up to about 400 ppm, up to about 300 ppm, up to about 200 ppm, up to about 100 ppm, up to about 50 ppm or less nitrogen.

A minimum amount of nitrogen in a composition of the invention may be at least 1 ppm, at least 5 ppm or at least 10 ppm.

Thus, a composition of the invention may comprise from 1 ppm to 1000 ppm nitrogen, from 1 ppm to 500 ppm nitrogen, from 1 ppm to 100 ppm nitrogen, from 5 ppm to 1000 ppm nitrogen, from 5 ppm to 500 ppm nitrogen, from 5 ppm to 100 ppm nitrogen, from 10 ppm to 1000 ppm nitrogen, from 10 ppm to 500 ppm nitrogen or from 10 ppm to 100 ppm nitrogen.

The amounts expressed in ppm represent the total amount of nitrogen in the composition.

A composition of the invention may comprise one or more of rebaudioside A, rebaudioside B, rebaudioside C, rebaudioside D, rebaudioside E, rebaudioside F, rebaudioside M, stevioside, dulcoside A, rubusoside or steviolbioside.

A composition of the invention may comprise at least 80% on a dry weight basis of one steviol glycoside, for example rebaudioside A, rebaudioside D or rebaudioside M. A composition of the invention may comprise at least 85% on a dry weight basis of one steviol glycoside, for example rebaudioside A, rebaudioside D or rebaudioside M. A composition of the invention may comprise at least 90% on a dry weight basis of one steviol glycoside, for example rebaudioside A, rebaudioside D or rebaudioside M. A composition of the invention may comprise at least 95% on a dry weight basis of one steviol glycoside, for example rebaudioside A, rebaudioside D or rebaudioside M. A composition of the invention may comprise at least 97% on a dry weight basis of one steviol glycoside, for example rebaudioside A, rebaudioside D or rebaudioside M. A composition of the invention may comprise at least 98% on a dry weight basis of one steviol glycoside, for example rebaudioside A, rebaudioside D or rebaudioside M. A composition of the invention may comprise at least 99% on a dry weight basis of one steviol glycoside, for example rebaudioside A, rebaudioside D or rebaudioside M.

The steviol glycoside present in a composition of the invention in an amount of at least 80% on a dry weight basis may be any one of rebaudioside A, rebaudioside B, rebaudioside C, rebaudioside D, rebaudioside E, rebaudioside F, rebaudioside M, stevioside, dulcoside A, rubusoside or steviolbioside. Preferably the steviol glycoside is rebaudioside A, rebaudioside D or rebaudioside M.

Thus, a composition of the invention may comprise rebaudioside A in an amount of at least 80% on a dry weight basis, at least 85% on a dry weight basis, at least 90% on a dry weight basis, at least 95% on a dry weight basis, at least 97% on a dry weight basis, at least 98% on a dry weight basis or at least 99% on a dry weight basis of at least one steviol glycoside and, in addition a non-zero amount of nitrogen up to a maximum of amount of 1000 ppm, for example up to a maximum of amount of 500 ppm, for example up to a maximum of amount of 100 ppm, for example up to a maximum amount of 50 ppm.

Thus, a composition of the invention may comprise rebaudioside D in an amount of at least 80% on a dry weight basis, at least 85% on a dry weight basis, at least 90% on a dry weight basis, at least 95% on a dry weight basis, at least 97% on a dry weight basis, at least 98% on a dry weight basis or at least 99% on a dry weight basis of at least one steviol glycoside and, in addition a non-zero amount of nitrogen up to a maximum of amount of 1000 ppm, for example up to a maximum of amount of 500 ppm, for example up to a maximum of amount of 100 ppm, for example up to a maximum amount of 50 ppm.

Thus, a composition of the invention may comprise rebaudioside M in an amount of at least 80% on a dry weight basis, at least 85% on a dry weight basis, at least 90% on a dry weight basis, at least 95% on a dry weight basis, at least 97% on a dry weight basis, at least 98% on a dry weight basis or at least 99% on a dry weight basis of at least one steviol glycoside and, in addition a non-zero amount of nitrogen up to a maximum of amount of 1000 ppm, for example up to a maximum of amount of 500 ppm, for example up to a maximum of amount of 100 ppm, for example up to a maximum amount of 50 ppm.

The method for preparing, for example purifying, a steviol glycoside composition as provided by the invention comprises crystallizing steviol glycosides from an aqueous solution comprising steviol glycosides. This step allows a significant reduction in the amount of nitrogen.

For the purposes of this invention an "aqueous solution" is one which comprises substantially no organic solvent. Thus, an aqueous solution may be one where substantially the only solvent is water (i.e low or trace amounts of other solvents may be present).

Accordingly, the invention provides a method for preparing, such as purifying a steviol glycoside composition, which method comprises crystallizing steviol glycosides from water. Crystallization from an organic solvent, such as ethanol, does not allow a reduction in the amount of nitrogen.

A method of the invention may thus comprise:

providing a steviol glycoside composition (a first steviol glycoside composition);

combining the steviol glycoside composition with water to form a steviol glycoside solution; and crystallizing a steviol glycoside composition (a second steviol glycoside composition) from the steviol glycoside solution.

The steviol glycoside composition produced in this method (the second steviol glycoside composition) comprises less nitrogen than the starting (first) steviol glycoside composition.

Accordingly, the invention provides a method for reducing the nitrogen content of a steviol glycoside composition, which method comprises crystallizing steviol glycosides from a solution of water comprising steviol glycosides and nitrogen.

Such a method may comprise:

providing a steviol glycoside composition (a first steviol glycoside composition) which comprises nitrogen;

combining the steviol glycoside composition with water to form a steviol glycoside solution; and crystallizing a steviol glycoside composition (a second steviol glycoside composition) from the solution, thereby to reduce the amount of nitrogen in the steviol glycoside composition (the first steviol glycoside composition).

The steviol glycoside composition produced in this method (the second steviol glycoside composition) comprises less nitrogen than the starting (first) steviol glycoside composition.

The crystallization step may be carried out at a pH of 6.0 or higher, at a pH of 7.0 or higher, at a pH of 8.0, at a pH of about 9.0 or higher.

A method of the invention allows a steviol glycoside composition (the second steviol glycoside composition identified above) to be achieved that comprises nitrogen in an amount of no more than about 1000 ppm, no more than 900 ppm, no more than about 800 ppm, no more than about 700 ppm, no more than about 600 ppm, no more than about 500 ppm, no more than about 400 ppm, no more than about 300 ppm, no more than about 200 ppm, no more than about 100 ppm or no more than about 50 ppm or less.

The composition may comprise a non-zero amount of nitrogen, such as at least 1 ppm, at least 5 ppm or at least 10 ppm nitrogen.

In the method of the invention, one or more of the steviol glycosides (in a starting or first steviol glycoside composition) may be fermentatively produced. That is to say, the steviol glycoside composition to be purified may be one derived from a fermentation broth. A fermentation broth may be subject to one or more of a solid/liquid separation, a cell disruption step, a chromatography step, a concentration step, a drying step or a crystallization step prior to the crystallization step according to the method of the present invention, which is typically a recrystallization step.

Typically, the method of the invention is carried out as a second or further crystallization, for example a recrystallization, such as a polish crystallization. A first crystallization may be used to recover steviol glycosides, i.e. to increase the amount of steviol glycosides in a composition. Typically, however, the method of the invention relates to a crystallization which is carried out using material with a high level of steviol glycosides with the aim of reducing nitrogen, not further concentrating the amount of steviol glycosides.

A first crystallization may be used to recover steviol glycosides and is typically carried out using an organic solvent to recover a higher purity steviol glycoside composition from a lower purity steviol glycoside composition.

The a method of the invention may comprise a step of providing a first steviol glycoside composition by crystallization, typically of fermentatively-produced steviol glycosides, optionally in an organic solvent.

Typically in a method of the invention, a steviol glycoside composition, such as a low purity steviol glycoside composition is combined with an organic solvent to form a low purity steviol glycoside solution. The organic solvent optionally may further comprise water in an amount up to about 25% by weight. For example, in particular embodiments the organic solvent may further comprise water in an amount from about 3% to about 20% by weight. Non-limiting examples of organic solvents include alcohol, acetone, acetonitrile, and ethyl acetate. Alcohol, as used herein, refers to any straight, branched, or cyclic; substituted or unsubstituted alkyl, alkenyl, or alkynyl group attached to at least one hydroxyl moiety. Non-limiting examples of alcohols include ethanol, methanol, isopropanol, 1-propanol, 1-butanol, 2-butanol, tert-butanol, and isobutanol.

In particular, the organic solvent may comprise a mixture of water and at least one organic solvent. In another exemplary embodiment, the at least one organic solvent comprises an alcohol, the alcohol comprising ethanol, methanol, or mixtures thereof.

In both crystallization according to the invention and any prior crystallization, the steviol glycoside solution may comprise the solvent and steviol glycoside composition in a weight ratio ranging from about 15 to about 4 parts solvent to about 1 part steviol glycoside.

Both crystallization according to the invention and any prior crystallization may be carried out at any suitable temperature. Crystallization may further comprise cooling the steviol glycoside solution. Generally, the steviol glycoside solution may be cooled to a temperature suitable for precipitation of the steviol glycosides from the steviol glycoside solution.

Both crystallization according to the invention and any prior crystallization may be allowed to take place for a length of time sufficient to obtain a desirable yield of the steviol glycoside composition from the steviol glycoside solution. For example, crystallization of the steviol glycoside solution may proceed from about 0.5 hours to about 120 hours (5 days), about 12 hours to about 96 hours (4 days), about 24 hours (1 day) to about 72 hours (3 days) or for any length of time there between.

After crystallization using organic solvent of a lower purity steviol glycoside solution, a higher purity steviol glycoside composition, for example a substantially pure steviol glycoside composition, may be obtained comprising, for example, rebaudioside A, rebaudioside D or rebaudioside M. A "substantially pure steviol glycoside composition" is used herein to refer to compositions comprising about 95% or greater by weight (on a dry basis) of steviol glycosides.

The total yield of the steviol glycoside composition may be, for example, about 25% or greater. Yield is used herein generally to refer to the mass obtained relative to the starting mass.

Subsequent recrystallization according to the present invention may then be used to reduce nitrogen content.

Both crystallization according to the invention and any prior crystallization may further comprise seeding the low purity steviol glycoside solution upon beginning the crystallization of the steviol glycoside solution. Seeding generally may be performed at the same temperature at which the crystallization is allowed to proceed.

Seeding of the low purity steviol glycoside solution generally may be performed, for example, by adding substantially pure crystals of rebaudioside A, rebaudioside D or rebaudioside M to the steviol glycoside solution in an amount sufficient to promote precipitation of the rebaudioside A, rebaudioside D or rebaudioside M and other steviol glycosides. An amount sufficient to promote precipitation generally may comprise a substantially pure rebaudioside A, rebaudioside D or rebaudioside M composition in an amount from about 0.0001% to about 1% by weight of the low purity steviol glycoside solution, from about 0.01% to about 1% by weight, or any amount therebetween.

Both crystallization according to the invention and any prior crystallization may further comprise steps of separating and washing the steviol glycoside compositions after their crystallization. The steviol glycoside composition may be separated from its supernatant by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any pressure, vacuum, or gravity filtration methods, that include without limitation, the use of belt, drum, nutsche type, leaf, plate, Rosenmund type, sparkler type, and bag filters and filter press. Operation of the solid-liquid separation device may be continuous, semi-continuous or in batch mode. The steviol glycoside composition also may be washed on the separation device using various organic solvents and mixtures thereof and can be partially or totally dried on the separation device using any number of gases, including, without limitation, nitrogen or argon, to evaporate residual liquid solvent. The steviol glycoside composition may be automatically or manually removed from the separation device using liquids, gases or mechanical means by either dissolving the solid or maintaining the solid form.

Both crystallization according to the invention and any prior crystallization may further comprise a step of drying the steviol glycoside composition. Suitable methods for drying such compositions are known to those skilled in the art and include, but are not limited to, the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer. In an exemplary embodiment, the steviol glycoside composition is dried using a nitrogen or argon purge to remove the residual solvent at a temperature in a range from about 40° C. to about 60° C. for a period of time from about 5 hours to about 5 days, from about 1 day to about 4 days, from about 2 days to about 3 days, or for any length of time there between.

The steviol glycoside composition used as starting material for use in a method of the invention (and resulting from a method of the invention) may comprise one or more of any one of rebaudioside B, rebaudioside C, rebaudioside D, rebaudioside F, rebaudioside M, stevioside, dulcoside A, rubusoside or steviolbioside.

The steviol glycoside starting composition invention, which is used to generate the aqueous solution on which crystallization or recrystallization is carried out may comprise at least 80% on a dry weight basis of at least one steviol glycoside, for example at least 95% on a dry weight basis of at least one steviol glycoside, such as at least 90% or at least 95% of rebaudioside A, at least 90% or at least 95% of rebaudioside D or at least 90% or at least 95% of rebaudioside M.

The steviol glycosides used in the invention may be fermentatively produced, for example derived from a recombinant host capable of producing a steviol glycoside. For example, a suitable recombinant host may be capable of producing one or more of, for example, steviol-13-monoside, steviol-19-monoside, 13-[(β-D-Glucopyranosyl)oxy) kaur-16-en-18-oic acid 2-O-β-D-glucopyranosyl-β-D-glucopyranosyl ester, rubusoside, stevioside, steviol-19-diside, steviolbioside, rebA, rebE, rebD or rebM.

A suitable recombinant host may comprise one or more recombinant nucleic acid sequences encoding one or more polypeptides having UDP-glycosyltransferase (UGT) activity.

For the purposes of this invention, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIG. 1 sets out a schematic diagram of steviol glycoside formation.

A recombinant host may thus comprise one or more recombinant nucleic acid sequences encoding one or more of:

(i) a polypeptide having UGT74G1 activity;
(ii) a polypeptide having UGT2 activity;
(ii) a polypeptide having UGT85C2 activity; and
(iii) a polypeptide having UGT76G1 activity.

A recombinant host may comprise a nucleotide sequence encoding a polypeptide capable of catalyzing the addition of a C-13-glucose to steviol. That is to say, a recombinant yeast suitable for use in a method of the invention may comprise a UGT which is capable of catalyzing a reaction in which steviol is converted to steviolmonoside.

Such a recombinant host may comprise a nucleotide sequence encoding a polypeptide having the activity shown by UDP-glycosyltransferase (UGT) UGT85C2, whereby the nucleotide sequence upon transformation of the yeast confers on that yeast the ability to convert steviol to steviolmonoside.

UGT85C2 activity is transfer of a glucose unit to the 13-OH of steviol. Thus, a suitable UGT85C2 may function as a uridine 5'-diphospho glucosyl: steviol 13-OH transferase, and a uridine 5'-diphospho glucosyl: steviol-19-0-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant host may comprise a nucleotide sequence encoding a polypeptide which has UGT2 activity.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-0-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-O-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D. However, a functional UGT2 polypeptide typically does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl: steviol-13-0-glucoside transferase, transferring a rhamnose moiety to the C-2' of the 13-O-glucose of the acceptor molecule, steviol.

A recombinant host may comprise a nucleotide sequence encoding a polypeptide having UGT activity may comprise a nucleotide sequence encoding a polypeptide capable of catalyzing the addition of a C-19-glucose to steviolbioside. That is to say, a recombinant host may comprise a UGT which is capable of catalyzing a reaction in which steviolbioside is converted to stevioside. Accordingly, such a recombinant host may be capable of converting steviolbioside to stevioside. Expression of such a nucleotide sequence may confer on the recombinant yeast the ability to produce at least stevioside.

A recombinant host may thus also comprise a nucleotide sequence encoding a polypeptide having the activity shown by UDP-glycosyltransferase (UGT) UGT74G1, whereby the nucleotide sequence upon transformation of the yeast confers on the cell the ability to convert steviolbioside to stevioside.

Suitable UGT74G1 polypeptides may be capable of transferring a glucose unit to the 13-OH or the 19-OOOH, respectively, of steviol. A suitable UGT74G1 polypeptide may function as a uridine 5'-diphospho glucosyl: steviol 19-OOOH transferase and a uridine 5'-diphospho glucosyl: steviol-13-O-glucoside 19-OOOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant host may comprise a nucleotide sequence encoding a polypeptide capable of catalyzing glucosylation of the C-3' of the glucose at the C-13 position of stevioside. That is to say, a recombinant yeast suitable for use in a method of the invention may comprise a UGT which is capable of catalyzing a reaction in which stevioside is converted to rebaudioside A. Accordingly, such a recombinant yeast may be capable of converting stevioside to rebaudioside A. Expression of such a nucleotide sequence may confer on the yeast the ability to produce at least rebaudioside A.

A recombinant host may thus also comprise a nucleotide sequence encoding a polypeptide having the activity shown by UDP-glycosyltransferase (UGT) UGT76G1, whereby the nucleotide sequence upon transformation of a yeast confers on that yeast the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-O-1,2 glucoside C-3 ' glucosyl transferase and a uridine 5'-diphospho glucosyl: steviol-19-O-glucose, 13-O-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM.

A recombinant host typically comprises nucleotide sequences encoding at least one polypeptide having UGT1 activity, at least one polypeptide having UGT2 activity, least one polypeptide having UGT3 activity and at least one polypeptide having UGT4 activity. One or more of these nucleic acid sequences may be recombinant. A given nucleic acid may encode a polypeptide having one or more of the above activities. For example, a nucleic acid encode for a polypeptide which has two, three or four of the activities set out above. Preferably, a recombinant yeast for use in the method of the invention comprises UGT1, UGT2 and UGT3 and UGT4 activity. Suitable UGT1, UGT2, UGT3 and UGT4 sequences are described in Table 1 of WO2015/007748.

A recombinant host may comprise two or more nucleic acid sequences encoding a polypeptide having any one UGT activity, for example UGT1, 2, 3 or 4, activity. Where a recombinant host comprises two or more nucleic acid sequence encoding a polypeptide having any one UGT activity, those nucleic acid sequences may be the same or different and/or may encode the same or different polypeptides. In particular, a recombinant host may comprise a nucleic acid sequence encoding a two different UGT2 polypeptides.

A recombinant host may comprise one or more recombinant nucleotide sequence(s) encoding one of more of:
a polypeptide having ent-copalyl pyrophosphate synthase activity;
a polypeptide having ent-Kaurene synthase activity;
a polypeptide having ent-Kaurene oxidase activity; and
a polypeptide having kaurenoic acid 13-hydroxylase activity.

For the purposes of this invention, a polypeptide having ent-copalyl pyrophosphate synthase (EC 5.5.1.13) is capable of catalyzing the chemical reaction:

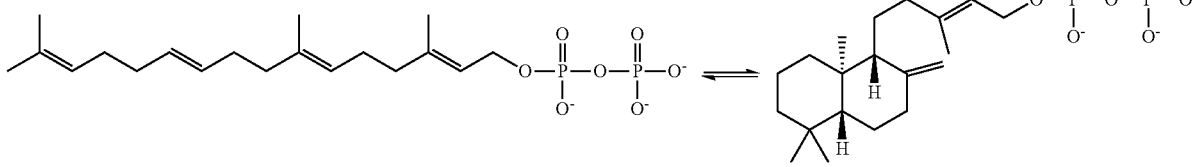

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing).

Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this invention, a polypeptide having ent-kaurene synthase activity (EC 4.2.3.19) is a polypeptide that is capable of catalyzing the chemical reaction:

ent-copalyl diphosphate ⇌ ent kaurene+diphosphate 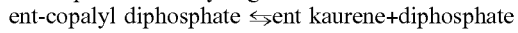

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in a recombinant host of the invention may encode a polypeptide having ent-copalyl pyrophosphate synthase activity and ent-kaurene synthase activity. Alternatively, the two activities may be encoded two distinct, separate nucleotide sequences.

For the purposes of this invention, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the invention, a polypeptide having kaurenoic acid 13-hydroxylase activity (EC 1.14.13) is one which is capable of catalyzing the formation of steviol (ent-kaur-16-en-13-ol-19-oic acid) using NADPH and $O_2$. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host may comprise a recombinant nucleic acid sequence encoding a polypeptide having NADPH-cytochrome p450 reductase activity. That is to say, a recombinant host of the invention may be capable of expressing a nucleotide sequence encoding a polypeptide having NADPH-cytochrome p450 reductase activity. For the purposes of the invention, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the eukaryotic cell from a FAD- and FMN-containing enzyme NADPH:cytochrome P450 reductase (POR; EC 1.6.2.4).

In a recombinant host, the ability of the host to produce geranylgeranyl diphosphate (GGPP) may be upregulated. Upregulated in the context of this invention implies that the recombinant host produces more GGPP than an equivalent non-recombinant host.

Accordingly, a recombinant host may comprise one or more nucleotide sequence(s) encoding hydroxymethylglutaryl-CoA reductase, farnesyl-pyrophosphate synthetase and geranylgeranyl diphosphate synthase, whereby the nucleotide sequence(s) upon transformation of a host confer(s) on that host the ability to produce elevated levels of GGPP. Thus, a recombinant host according to the invention may comprise one or more recombinant nucleic acid sequence(s) encoding one or more of hydroxymethylglutaryl-CoA reductase, farnesyl-pyrophosphate synthetase and geranylgeranyl diphosphate synthase.

Accordingly, a recombinant host may comprise nucleic acid sequences encoding one or more of:
a polypeptide having hydroxymethylglutaryl-CoA reductase activity;
a polypeptide having farnesyl-pyrophosphate synthetase activity; and A recombinant host may be, for example, an multicellular organism or a cell thereof or a unicellular organism. A host may be a prokaryotic, archaebacterial or eukaryotic host cell.

A prokaryotic host cell may, but is not limited to, a bacterial host cell. An eukaryotic host cell may be, but is not limited to, a yeast, a fungus, an amoeba, an algae, an animal, an insect host cell.

An eukaryotic host cell may be a fungal host cell. "Fungi" include all species of the subdivision *Eumycotina* (Alexopoulos, C. J., 1962, In: Introductory Mycology, John Wiley & Sons, Inc., New York). The term fungus thus includes among others filamentous fungi and yeast.

"Filamentous fungi" are herein defined as eukaryotic microorganisms that include all filamentous forms of the subdivision *Eumycotina* and *Oomycota* (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podosporus, Pycnoporus, Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

An eukaryotic host cell may be a yeast cell. Preferred yeast host cells may be selected from the genera: *Saccharomyces* (e.g., *S. cerevisiae, S. bayanus, S. pastorianus, S. carlsbergensis*), *Brettanomyces, Kluyveromyces, Candida* (e.g., *C. krusei, C. revkaufi, C. pulcherrima, C. tropicalis, C. utilis*), *Issatchenkia* (eg. *I. orientalis*) *Pichia* (e.g., *P. pastoris*), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), *Yamadazyma*.

Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli* (e.g., strains DH 1 OB, Stbl2, DH5-alpha, DB3, DB3.1), DB4, DB5, JDP682 and ccdA-over (e.g., U.S. application Ser. No. 09/518, 188))), *Streptomyces, Erwinia, Klebsiella, Serratia* (e.g., *S. marcessans*), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., Choroflexus bacteria (e.g., *C. aurantiacus*), Chloronema (e.g., *C. gigateum*)), green sulfur bacteria (e.g., *Chlorobium* bacteria (e.g., *C. limicola*), Pelodictyon (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), *Rhodobacter* (e.g. *R. sphaeroides, R. capsulatus*), and Rhodomicrobium bacteria (e.g., *R. vanellii*)).

Host Cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

A recombinant host may be able to grow on any suitable carbon source known in the art and convert it to a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP1499708B1, WO2006096130 or WO04/099381.

Standard genetic techniques, for the construction of such recombinant hosts, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265, 186.

A process for the preparation of a steviol glycoside may comprise fermenting a recombinant host as described herein which is capable of producing at least one steviol glycoside in a suitable fermentation medium, and optionally recovering the steviol glycoside.

The fermentation medium used in the process for the production of a steviol glycoside may be any suitable fermentation medium which allows growth of a particular eukaryotic host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, sucrose, lactose, fatty acids, triglycerides and glycerol. Preferably, the fermentation medium also comprises a nitrogen source such as ureum, or an ammonium salt such as ammonium sulphate, ammonium chloride, ammoniumnitrate or ammonium phosphate.

The fermentation process according to the present invention may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicelluose or pectin is used as a carbon source in the fermentation process, where it may be necessary to add hydrolytic enzymes, such as cellulases, hemicellulases or pectinases to hydrolyse the substrate.

The recombinant host used in the process for the preparation of a steviol glycoside may be any suitable recombinant host as defined herein above. It may be advantageous to use a recombinant eukaryotic recombinant host according to the invention in the process since most eukaryotic cells do not require sterile conditions for propagation and are insensitive to bacteriophage infections. In addition, eukaryotic host cells may be grown at low pH to prevent bacterial contamination.

The recombinant host may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a steviol glycoside according to the present invention may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present invention may also first be run under aerobic conditions and subsequently under anaerobic conditions.

The fermentation process may also be run under oxygen-limited, or micro-aerobical, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used.

The production of a steviol glycoside in the process may occur during the growth phase of the host cell, during the stationary (steady state) phase or during both phases. It may be possible to run the fermentation process at different temperatures.

The process for the production of a steviol glycoside may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a steviol glycoside according to the present invention may be carried out at any suitable pH value. If the recombinant host is a yeast, the pH in the fermentation medium preferably has a value of below 6, preferably below 5.5, preferably below 5, preferably below 4.5, preferably below 4, preferably below pH 3.5 or below pH 3.0, or below pH 2.5, preferably above pH 2. An advantage of carrying out the fermentation at these low pH values is that growth of contaminant bacteria in the fermentation medium may be prevented.

Such a process may be carried out on an industrial scale. The product of such a process is a fermentation broth comprising one or more steviol glycosides. Such a fermentation broth may be subject to one or more of a solid/liquid separation, a cell disruption step, a chromatography step, a concentration step and a drying step prior to crystallization according to the method of the present invention.

A composition according to the invention or a composition produced by the process according to the present invention may be used in any application known for such compounds. In particular, such a composition may for instance be used as a sweetener, for example in a food or a beverage. According to the invention therefore, there is provided a foodstuff, feed or beverage which comprises a composition of the invention or a composition produced by the process according to the present invention.

For example a composition of the invention or a composition produced by the process according to the present invention may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a steviol glycoside or a composition of the invention can be used as a sweetener not only for drinks, foodstuffs, and other products dedicated for human consumption, but also in animal feed and fodder with improved characteristics.

Accordingly, the invention provides, inter alia, a foodstuff, feed or beverage which comprises a composition of the invention or a composition produced by the process according to the present invention.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

A composition of the invention or a composition produced by the process according to the present invention can be used in dry or liquid forms. It can be added before or after heat treatment of food products. The amount of the sweetener depends on the purpose of usage. It can be added alone or in the combination with other compounds.

A composition of the invention or a composition produced by the process according to the present invention may be blended with one or more further non-caloric or caloric sweeteners. Such blending may be used to improve flavour or temporal profile or stability. A wide range of both non-caloric and caloric sweeteners may be suitable for blending with a steviol glycoside or a composition of the invention. For example, non-caloric sweeteners such as mogroside, monatin, aspartame, acesulfame salts, cyclamate, sucralose, saccharin salts or erythritol. Caloric sweeteners suitable for blending with a steviol glycoside or a composition of the invention include sugar alcohols and carbohydrates such as sucrose, glucose, fructose and HFCS. Sweet tasting amino acids such as glycine, alanine or serine may also be used.

A composition of the invention or a composition produced by the process according to the present invention can be used in the combination with a sweetener suppressor, such as a natural sweetener suppressor. It may be combined with an umami taste enhancer, such as an amino acid or a salt thereof.

A composition of the invention or a composition produced by the process according to the present invention can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition of the invention or a composition produced by the process according to the present invention may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A composition of the invention or a composition produced by the process according to the present invention may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a composition of the invention or a composition produced by the process according to the present invention may be used as a sweetener not only for drinks, foodstuffs, and other products dedicated for human consumption, but also in animal feed and fodder with improved characteristics.

The examples of products where a composition of the invention or a composition produced by the process according to the present invention can be used as a sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions which incorporate a composition of the invention or a composition produced by the process according to the present invention can be made by any method known to those skilled in the art that provide homogenous even or homogeneous mixtures of the ingredients. These methods include dry blending, spray drying, agglomeration, wet granulation, compaction, co-crystallization and the like.

In solid form a composition of the invention or a composition produced by the process according to the present invention can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

A composition of the invention or a composition produced by the process according to the present invention may include various bulking agents, functional ingredients, colorants, flavors.

Embodiments of the Invention

1. A composition comprising one or more steviol glycosides which composition comprises nitrogen in an amount of no more than about 1000 ppm.
2. A composition comprising one or more steviol glycosides which composition comprises nitrogen in an amount of no more than about 100 ppm.
3. A composition according to embodiment 1 or 2, wherein the steviol glycosides are fermentatively produced.
4. A composition according to any one of the preceding embodiments which comprises one or more of any one of rebaudioside A, rebaudioside B, rebaudioside C, rebaudioside D, rebaudioside E, rebaudioside F, rebaudioside M, stevioside, dulcoside A, rubusoside or steviolbioside.
5. A composition according to any one of the preceding embodiments which comprises at least 80% on a dry weight basis of at least one steviol glycoside.
6. A composition according to any one of the preceding embodiments which comprises at least 95% on a dry weight basis of at least one steviol glycoside.
7. A method for preparing a steviol glycoside composition, which method comprises:
    providing a steviol glycoside composition;
    combining the steviol glycoside composition with water to form a steviol glycoside solution; and
    crystallizing a steviol glycoside composition from the steviol glycoside solution.
8. A method for reducing the nitrogen content of a steviol glycoside composition, which method comprises:
    providing a steviol glycoside composition which comprise nitrogen;
    combining the steviol glycoside composition with water to form a steviol glycoside solution; and
    crystallizing a steviol glycoside composition from the steviol glycoside solution, thereby to reduce the amount of nitrogen in the steviol glycoside composition.
9. A method according to embodiment 7 or 8, wherein the crystallization is carried out at pH6.0 or above.
10. A method according to any one of embodiments 7 to 9, wherein the crystallization is a recrystallization step.
11. A method according to any one of embodiments 7 to 9, wherein the starting steviol glycoside composition comprises at least 95% on a dry weight basis of at least one steviol glycoside.

12. A method according to embodiment 7 or 8, wherein the crystallization is carried out at pH8.0 or above.
13. A method according to any one of embodiments 7 to 12, wherein the resulting steviol glycoside composition comprises nitrogen in an amount of no more than about 1000 ppm.
14. A method according to embodiment 13, wherein the resulting steviol glycoside composition comprises nitrogen in an amount of no more than about 100 ppm.
15. A method according to any one of embodiments 7 to 14, wherein the steviol glycosides are fermentatively produced.
16. A according to any one of embodiments 7 to 15, wherein the resulting steviol glycoside composition comprises one or more of any one of rebaudioside A, rebaudioside B, rebaudioside C, rebaudioside D, rebaudioside E, rebaudioside F, rebaudioside M, stevioside, dulcoside A, rubusoside or steviolbioside.
17. A method according to any one of embodiments 7 to 16, wherein the resulting steviol glycoside composition comprises at least 80% on a dry weight basis of at least one steviol glycoside.
18. A method according to embodiment 17, wherein the resulting steviol glycoside composition comprises at least 95% on a dry weight basis of at least one steviol glycoside.
19. A steviol glycoside composition obtainable by a method according to any one of embodiments 7 to 18.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

Example 1: Nitrogen Reduction in a Steviol Glycoside Composition by Recrystallization in Water A fermentatively-produced rebaudioside A-containing steviol glycoside composition was produced by fermentation of a Yarrowia lipolitica strain based on ML14869 as described in co-pending patent application no. PCT/EP2016/055734. A UGT2 variant, UGT2_5 b, was added to ML14869, as is described in Example 15 of PCT/EP2016/055734 (UGT2_5 b has the open reading frame having the sequence set out in SEQ ID NO: 11 of PCT/EP2016/055734) to arrive at the final strain which was used.

The strain was fermented using the procedure set out in WO2013/110673 and WO2015/007748 (see Table A, below).

TABLE A

Composition of fermentation medium

| Raw material | | Final Concentration (g/kg) |
|---|---|---|
| Glucose, 1 ag | $C_6H_{12}O_6 \cdot 1H_2O$ | 66 |
| Ammonium sulphate | $(NH_4)_2SO_4$ | 1 |
| Potassium dihydrogen phosphate | $KH_2PO_4$ | 20 |
| Magnesium sulphate | $MgSO_4 \cdot 7H_2O$ | 10 |
| Trace element solution | — | 16 |
| Vitamin solution | — | 16 |

The fermentation broth was then subjected to the following steps: centrifugation, heat shock, polish filtration, chromatography over an HP20 column, concentration/evaporation, cation exchange, anion exchange and then the final material was spray-dried.

The resulting dried fermentatively-derived steviol glycoside containing material comprising rebaudioside A was then redissolved in 92% ethanol and then crystallized to generate a composition comprising about 95% rebaudioside A by dry weight.

This material was dissolved to a concentration of 120 g/kg in Milli Q water of 20° C. while vigorously mixing with overhead stirrer with a 5 cm diameter straight bladed turbine agitator. When completely dissolved, the pH was adjusted with 0.5 M sodium hydroxide. This liquid was transferred to a double walled vessel which was cooled to 3° C. and then stirred from above with a 5 cm diameter straight-bladed turbine agitator at 160 rpm for 16 hours.

The formed crystals were transformed into centrifuge pots and centrifuged for 30 minutes at 4000 g. The mother liquid was removed and the crystals re-slurried with 1 bed volume of Milli Q water. This was centrifuged for 30 minutes at 4000 g and water was removed. The washing step was repeated two times, after which the crystals were removed and dried for 16 hours at 70° C. at 150 mbar.

The dried crystals were dissolved to a concentration of 125 g/kg and spray-dried. Nitrogen content was determined by Kjeldahl method.

The results are shown in Table 1 below and demonstrate that the recrystallization in water has a pronounced influence on the nitrogen removal and may be further improved by controlling pH. This allows the nitrogen amount of a steviol glycoside composition to be greatly reduced.

TABLE 1

Nitrogen values by water crystallizations at different pHs

| pH | N start (prior to polish crystallization) | N end (following polish crystallization) |
|---|---|---|
| 6 | 800-2000 mg/kg | 70 mg/kg |
| 8 | 800-2000 mg/kg | 50 mg/kg |
| 9 | 800-2000 mg/kg | 40 mg/kg |

The invention claimed is:
1. A method for preparing a steviol glycoside composition, which method comprises:
   providing a fermentation broth comprising a steviol glycoside;
   subjecting the fermentation broth to a solid-liquid separation and a crystallization, to yield a first steviol glycoside composition;
   combining the first steviol glycoside composition with water to form a steviol glycoside solution; and
   recrystallizing, at pH 7.0 or above, a second steviol glycoside composition from the steviol glycoside solution, wherein:
      the resulting second steviol glycoside composition comprises less nitrogen than the first steviol glycoside composition;
      the nitrogen in the resulting second steviol glycoside composition is no more than 800 ppm; and
      the resulting second steviol glycoside composition comprises at least 80% on a dry weight basis of at least one steviol glycoside selected from the group consisting of rebaudioside A, rebaudioside D, and rebaudioside M.

2. The method according to claim 1, wherein the first steviol glycoside composition comprises at least 95% on a dry weight basis of at least one steviol glycoside.

3. The method according to claim 2, wherein the crystallization is carried out at pH 8.0 or above.

4. The method according to claim 3, wherein the resulting second steviol glycoside composition comprises nitrogen in an amount of no more than about 500 ppm.

5. The method according to claim 4, wherein the resulting second steviol glycoside composition comprises nitrogen in an amount of no more than about 100 ppm.

6. The method according to claim 5, wherein the resulting second steviol glycoside composition further comprises one or more of any one of rebaudioside B, rebaudioside C, rebaudioside E, rebaudioside F, stevioside, dulcoside A, rubusoside or steviolbioside.

7. The method according to claim 6, wherein the resulting second steviol glycoside composition comprises at least 95% on a dry weight basis of at least one steviol glycoside.

8. The method according to claim 7, wherein the first steviol glycoside composition comprises at least 80% on a dry weight basis of at least one steviol glycoside.

9. The method according to claim 7, wherein the crystallization is carried out at pH 9.0 or above.

10. The method according to claim 7, wherein the resulting second steviol glycoside composition comprises nitrogen in an amount of no more than about 200 ppm.

11. The method according to claim 7, wherein the resulting second steviol glycoside composition comprises nitrogen in an amount of no more than about 50 ppm.

12. The method according to claim 7, wherein the resulting second steviol glycoside composition comprises at least 97% on a dry weight basis of rebaudioside A.

13. The method according to claim 7, wherein the resulting second steviol glycoside composition comprises at least 97% on a dry weight basis of rebaudioside D.

14. The method according to claim 7, wherein the resulting second steviol glycoside composition comprises at least 97% on a dry weight basis of rebaudioside M.

* * * * *